US010228306B2

(12) United States Patent
Kim et al.

(10) Patent No.: US 10,228,306 B2
(45) Date of Patent: Mar. 12, 2019

(54) SENSOR FOR MEASURING PARTICULATE MATTER WITH A BIAS VOLTAGE

(71) Applicant: HYUNDAI MOTOR COMPANY, Seoul (KR)

(72) Inventors: Dong-gu Kim, Suwon-si (KR); Sang-Hyeok Yang, Suwon-si (KR)

(73) Assignee: Hyundai Motor Company, Seoul (KR)

( * ) Notice: Subject to any disclaimer, the term of this patent is extended or adjusted under 35 U.S.C. 154(b) by 140 days.

(21) Appl. No.: 15/377,423

(22) Filed: Dec. 13, 2016

(65) Prior Publication Data

US 2018/0156693 A1    Jun. 7, 2018

(30) Foreign Application Priority Data

Dec. 7, 2016 (KR) .................. 10-2016-0165959

(51) Int. Cl.
*G01M 15/10* (2006.01)
*G01N 15/06* (2006.01)
*G01N 15/00* (2006.01)

(52) U.S. Cl.
CPC ...... *G01M 15/102* (2013.01); *G01N 15/0606* (2013.01); *G01N 15/0656* (2013.01); *G01N 2015/0046* (2013.01)

(58) Field of Classification Search
CPC ........... G01N 15/0656; G01N 15/0606; G01N 27/226; F01N 2560/05; F01N 13/008; G01M 15/102; F02D 41/1466
See application file for complete search history.

(56) References Cited

U.S. PATENT DOCUMENTS

| 6,634,210 | B1 * | 10/2003 | Bosch | G01N 15/0656 204/426 |
| 8,161,796 | B2 * | 4/2012 | Nair | G01N 15/0656 73/23.33 |
| 8,578,756 | B2 | 11/2013 | Suzuki | |
| 8,928,338 | B2 * | 1/2015 | Nelson | F02D 41/1466 324/464 |
| 9,134,216 | B2 * | 9/2015 | Hedayat | G01N 15/0656 |
| 9,389,163 | B2 * | 7/2016 | Hedayat | G01N 15/0656 |
| 9,494,508 | B2 | 11/2016 | Lee et al. | |
| 9,528,971 | B2 * | 12/2016 | Teranishi | G01N 33/0047 |
| 9,778,160 | B2 * | 10/2017 | Zhang | G01N 15/0656 |

(Continued)

FOREIGN PATENT DOCUMENTS

| JP | 2010525367 A | 7/2010 |
| JP | 2011247650 | 12/2011 |

(Continued)

*Primary Examiner* — Freddie Kirkland, III
(74) *Attorney, Agent, or Firm* — Lempia Summerfield Katz LLC (57) ABSTRACT

A sensor for measuring particulate matters is supplied with a bias voltage to form an electric field to increase an accumulated amount of particulate matters at a sensing unit. The sensor includes a sensing unit in which measurement electrodes and ground electrodes are disposed to alternate with one another in a housing fixed to an exhaust pipe. The measurement electrodes are electrically connected to one another, and the ground electrodes are electrically connected to one another. Bias electrodes are disposed between the ground electrodes to supply the bias voltage to the sensing unit. The bias electrodes are electrically connected to one other.

10 Claims, 13 Drawing Sheets

(56) References Cited

U.S. PATENT DOCUMENTS

| | | |
|---|---|---|
| 2008/0265870 A1 | 10/2008 | Nair et al. |
| 2009/0056416 A1* | 3/2009 | Nair .................. G01N 15/0656 73/28.01 |
| 2011/0283773 A1 | 11/2011 | Suzuki |
| 2012/0103057 A1 | 5/2012 | Kimata et al. |
| 2015/0020576 A1 | 1/2015 | Lee et al. |
| 2016/0223432 A1 | 8/2016 | Kubinski |

FOREIGN PATENT DOCUMENTS

| | | |
|---|---|---|
| JP | 5201193 | 6/2013 |
| JP | 2013205028 | 10/2013 |
| JP | 2016085132 A | 5/2016 |
| KR | 20100035682 | 4/2010 |
| KR | 20150010218 | 1/2015 |
| KR | 20150071771 | 6/2015 |
| KR | 101547446 B1 | 8/2015 |
| KR | 101593669 B1 | 2/2016 |

\* cited by examiner

SENSOR FOR MEASURING PARTICULATE MATTER WITH A BIAS VOLTAGE

CROSS-REFERENCE TO RELATED APPLICATIONS

This application claims priority to Korean Patent Application No. 10-2016-0165959, filed on Dec. 7, 2016, which is incorporated herein by reference in its entirety.

BACKGROUND

Field of the Disclosure

The disclosure relates to a sensor for measuring particulate matters (PMs) included in exhaust gas of a vehicle and, more particularly, to a sensor for measuring particulate matters with a bias voltage supplied to form an electric field to increase an accumulated amount of particulate matters at a sensing unit.

Description of Related Art

Exhaust gas of a vehicle includes various harmful materials. Emissions of the harmful materials are limited by various regulations.

For this purpose, the vehicle includes various sensors to monitor the emitted harmful substances.

As an example, the vehicle includes a sensor for measuring particulate matters (PMs) included in the exhaust gas. The sensor for measuring particulate matters is mounted in an exhaust pipe at a back end of a diesel particulate filter (DPF) to measure a concentration of the particulate matters in the exhaust gas, thereby determining whether the DPF fails.

Figure 1:
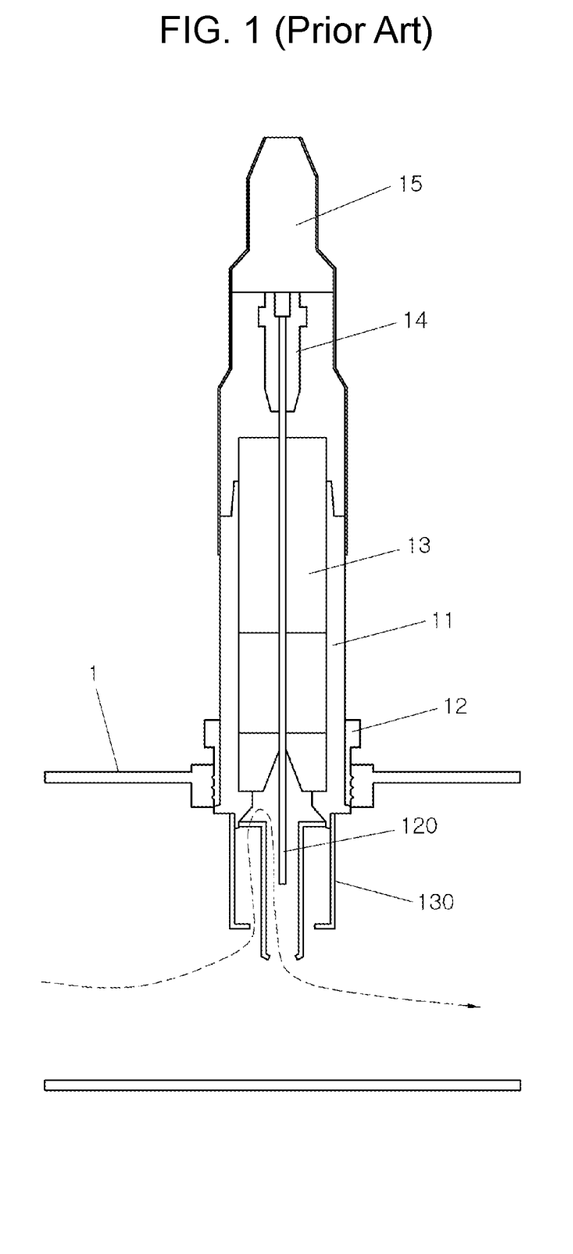
FIG. 1 is a cross-sectional view of a prior art sensor for measuring particulate matters.

A structure of the sensor for measuring particulate matters is described with reference to FIG. 1. A sensing unit 120 is mounted in a housing 11. The housing 11 is fixed to an exhaust pipe 1 by a lock nut 12. The inside of the housing 11 is provided with an insulator 13 for insulating the sensing unit 120. An upper end of the sensing unit 120 is fixed by a clam shell 14. An upper end of the sensor for measuring particulate matters is formed with Teflon 15 (PTFE). A lower end of the sensing unit 120 is exposed to the flowing exhaust gas. A lower end of the housing 11 is coupled with a protective tube 130 to introduce the exhaust gas flowing in the exhaust pipe 1 into the sensing unit 120.

Figure 2:
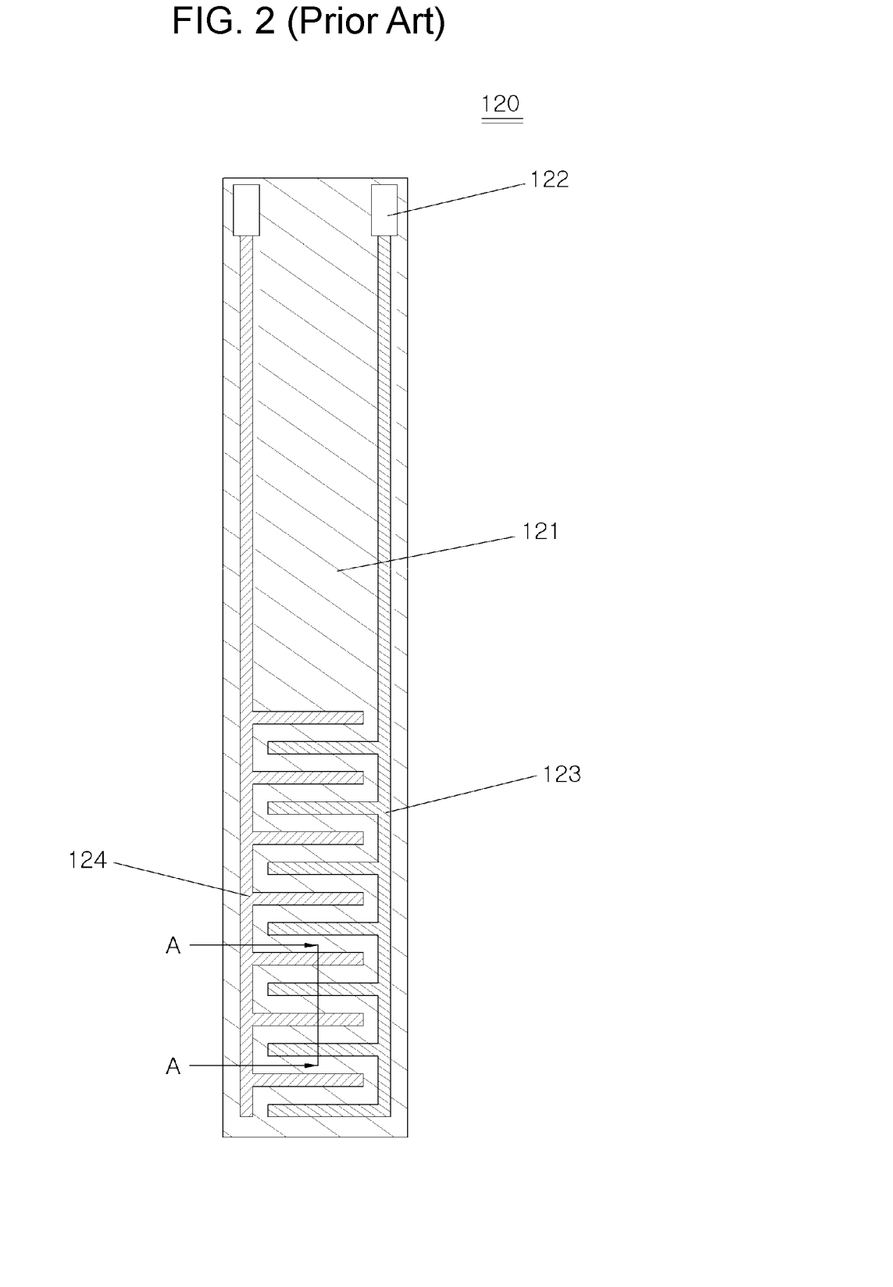
FIG. 2 is a plan view of a sensing unit of the prior art sensor of FIG. 1.
Figure 3:
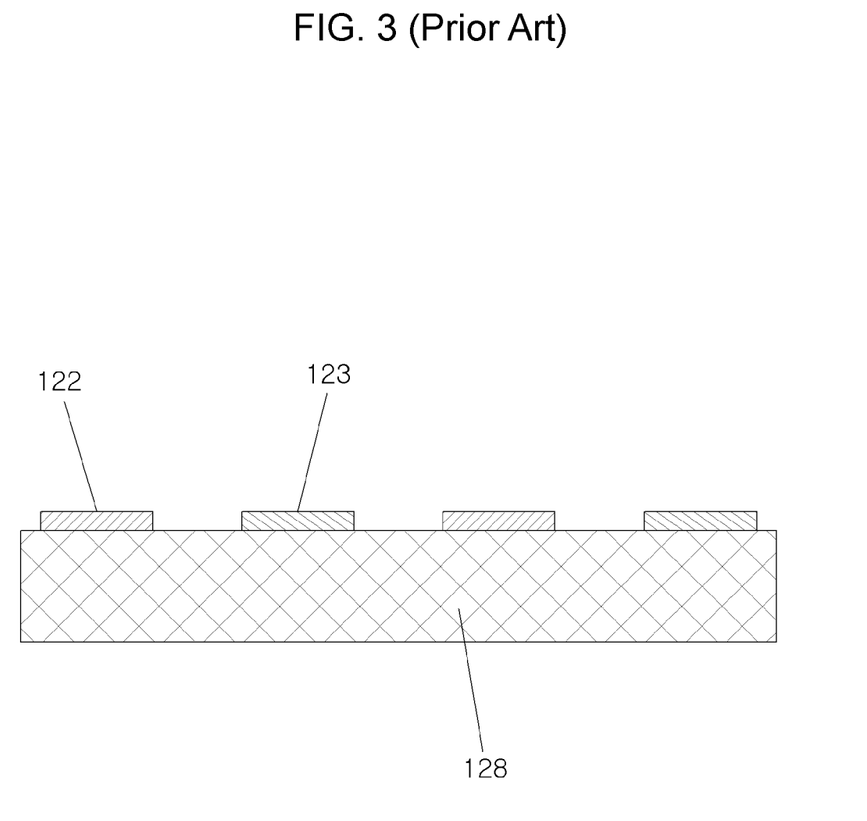
FIG. 3 is a cross-sectional view taken along line A-A of FIG. 2.
Figure 4:
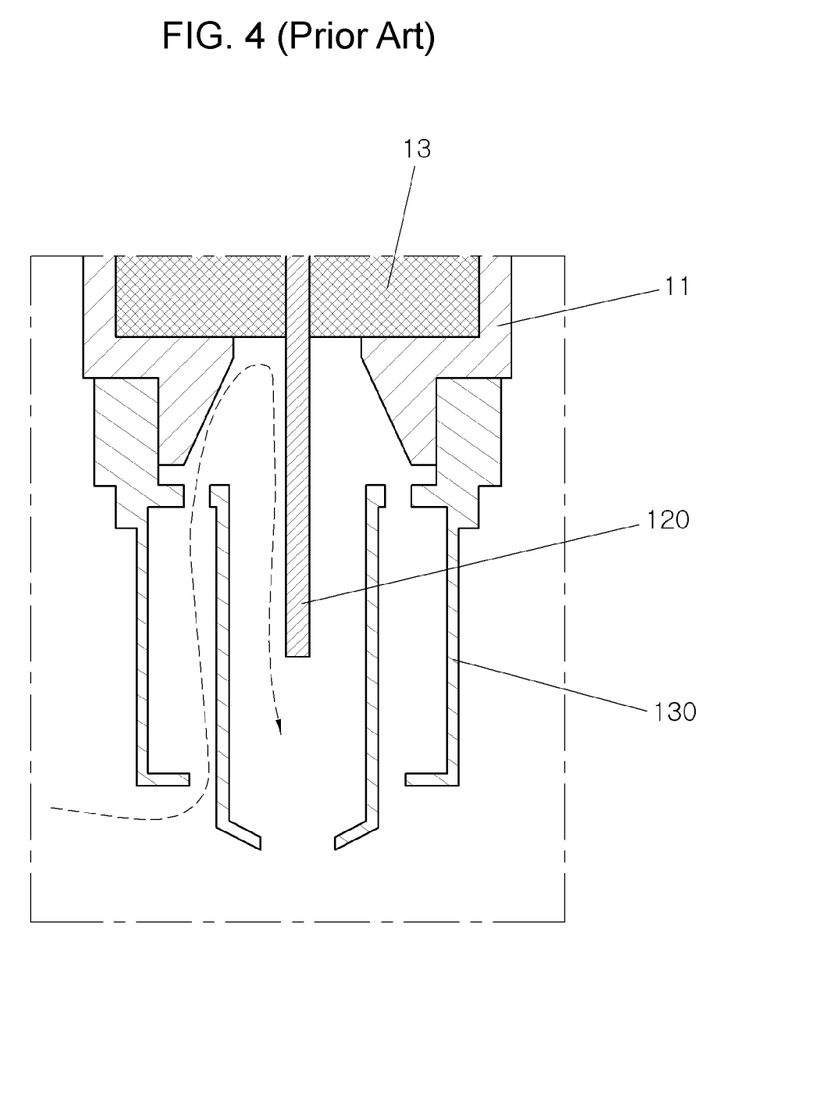
FIG. 4 is an enlarged cross-sectional view of main parts of the prior art sensor of FIG. 1.

As illustrated in FIG. 2, in the sensing unit 120, a measurement electrode 124 and a ground electrode 123 are formed on a substrate 121. Each of the measurement electrode 124 and the ground electrode 123 is electrically connected to an outside of the sensor for measuring particulate matters through a separate pad electrode 122.

The measurement electrodes 124 and the ground electrodes 123 are disposed to alternate with each other. One terminal of the measurement electrode 124 and one terminal of the ground electrode 123 are electrically connected to one another.

The sensor for measuring particulate matters measures the amount of particulate matters based on a change in capacitance as the particulate materials are accumulated on a surface of the sensing unit 120 by an armature formed between the measurement electrode 124 and the ground electrode 123.

Past sensors for measuring particulate matters undesirably increase the amount of particulate matters accumulated in the sensing unit 120 to measure the amount of particulate matters.

Further, the measurement electrode 124 and the ground electrode 123 are formed to be exposed to the exhaust gas, and therefore need to be made of platinum (Pt), an expensive material. As a result, sensors for measuring particulate matters are costly.

The sensing unit 120 is located inside the protective tube 130 fastened with the lower end of the housing 11, which is to reduce noise. If the sensing unit 120 is directly exposed to the exhaust gas, a noise signal is generated due to foreign materials included in the exhaust gas. To prevent this, the protective tube 130 is formed in a double tube form to prevent the sensing unit 120 from being directly exposed to the exhaust gas and pass the exhaust gas introduced into the protective tube 130 through the sensing unit 120.

SUMMARY OF THE DISCLOSURE

In accordance with one aspect, a sensor for measuring particulate matters uses a bias voltage to increase an amount of particulate matters accumulated on a sensor unit. A bias electrode is disposed at a portion of the sensor where the particulate matters are accumulated.

In accordance with another aspect, a sensor for measuring particulate matters uses a bias voltage to prevent foreign materials from being introduced into a sensing unit while exhaust gas in an exhaust pipe flows in the sensing unit.

In accordance with yet another aspect, a sensor for measuring particulate matters in exhaust gas with a bias voltage includes a sensing unit in which measurement electrodes and ground electrodes are disposed to alternate with one another in a housing fixed to an exhaust pipe. The measurement electrodes are electrically connected to one another and the ground electrodes are electrically connected to one another. Bias electrodes are disposed between the ground electrodes to supply the bias voltage to the sensing unit, and one terminal of the bias electrodes is electrically connected to each other.

The bias electrodes may be each disposed between the ground electrodes at the same height as the ground electrode. The measurement electrode may be disposed between the bias electrode and the ground electrode adjacent to one another at the same height as the bias electrode and the ground electrode. One terminal of the measurement electrodes may be electrically connected to one another.

The measurement electrode, the ground electrode, and the bias electrode may be formed in a ceramic layer.

The measurement electrode, the ground electrode, and the bias electrode may be made of molybdenum (Mo) as a material.

The bias electrode may be formed in the same pattern as the measurement electrode. The bias electrode may be located above the measurement electrode.

The measurement electrode and the ground electrode may be formed in a ceramic layer. The bias electrode may be formed on a surface of the ceramic layer.

The measurement electrode and the ground electrode may be made of molybdenum as a material. The bias electrode may be made of platinum (Pt) as a material.

In the sensing unit, a heater may be patterned on a layer disposed under a layer on which the measurement electrode, the ground electrode, and the bias electrode are formed to increase a temperature of the sensing unit. A layer under the layer on which the heater may be formed is provided with a temperature sensor measuring a temperature of the heater.

A protective tube having a cylindrical shape and formed with introduction holes that are disposed to be upwardly inclined along a circumference thereof, that penetrate through an inside of the protective tube from an outside thereof, and that are disposed at a predetermined interval along a circumference thereof, may be fastened with a lower end of the housing. The exhaust gas flowing in the exhaust pipe may flow in the sensing unit through the introduction hole.

The introduction hole may be disposed in a plurality of rows along a length direction of the protective tube.

DETAILED DESCRIPTION

Sensors for measuring particulate matters with a bias voltage are described in detail with reference to the accompanying drawings.

A sensor for measuring particulate matters with a bias voltage according to one embodiment includes a sensing unit 20 included in a housing 11. The sensing unit includes measurement electrodes 24 and ground electrodes 23 that are disposed to alternate with one another, in which the measurement electrodes are electrically connected to one another, the ground electrodes are electrically connected to one another, and bias electrodes 25 disposed between the ground electrodes 23 to supply a bias voltage to the sensing unit 20 are electrically connected to one another. The measurement electrode 24, the ground electrode 23, and the bias electrode 25 are not electrically connected to one another.

Figure 5:
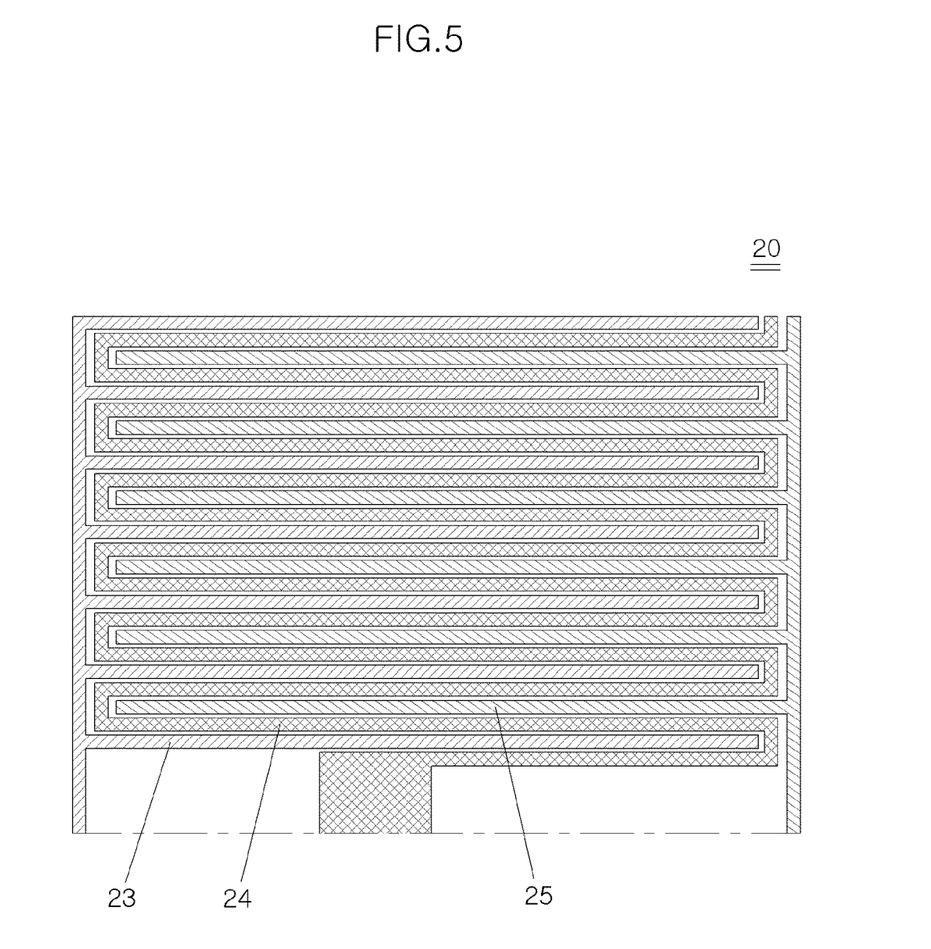
FIG. 5 is a plan view of a sensing unit of a sensor for measuring particulate matters with a bias voltage in accordance with one embodiment.
Figure 6:
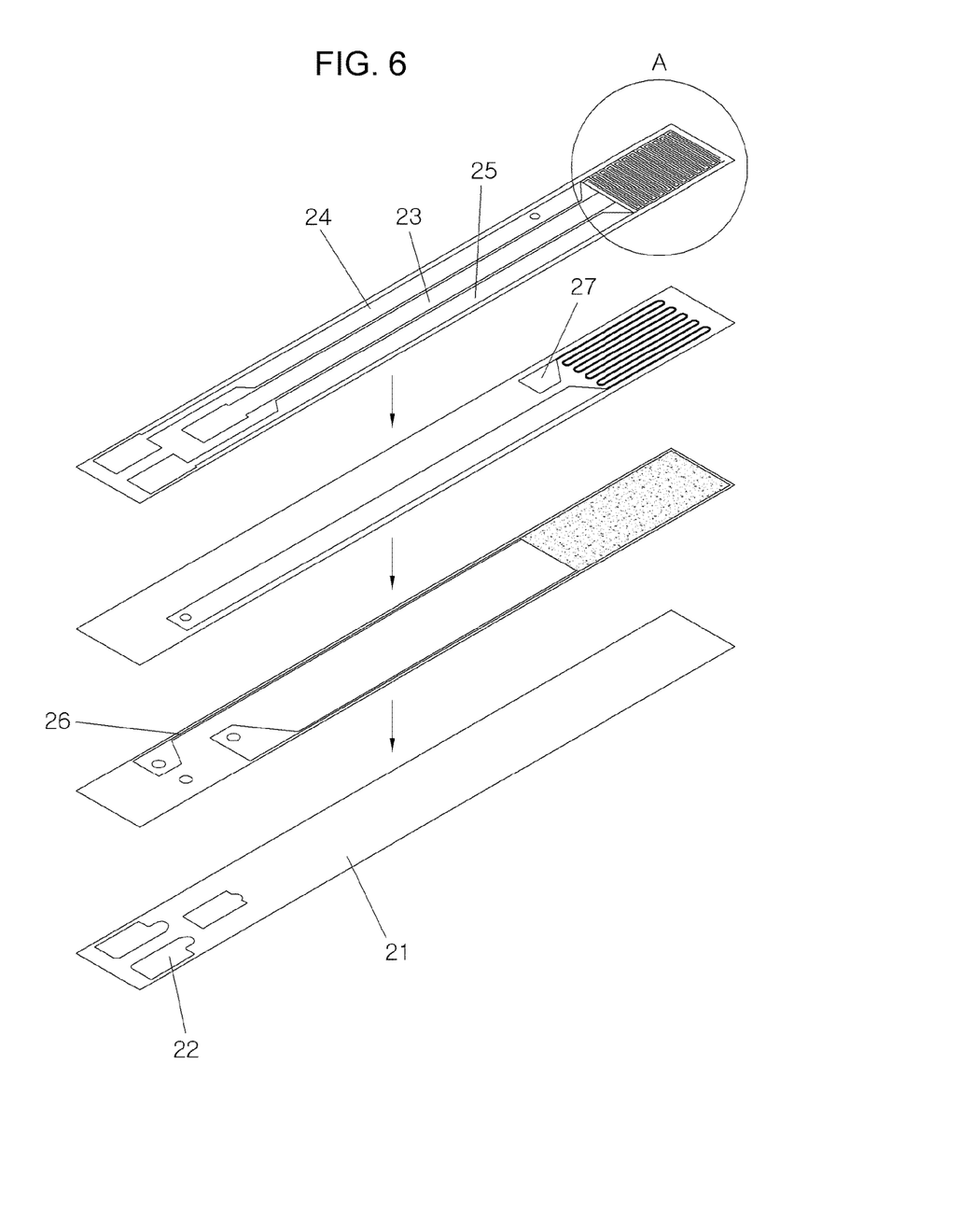
FIG. 6 is an exploded, perspective view of a sensing unit of a sensor for measuring particulate matters with a bias voltage in accordance with one embodiment, the sensing unit being illustrated in an unassembled state.
Figure 7:
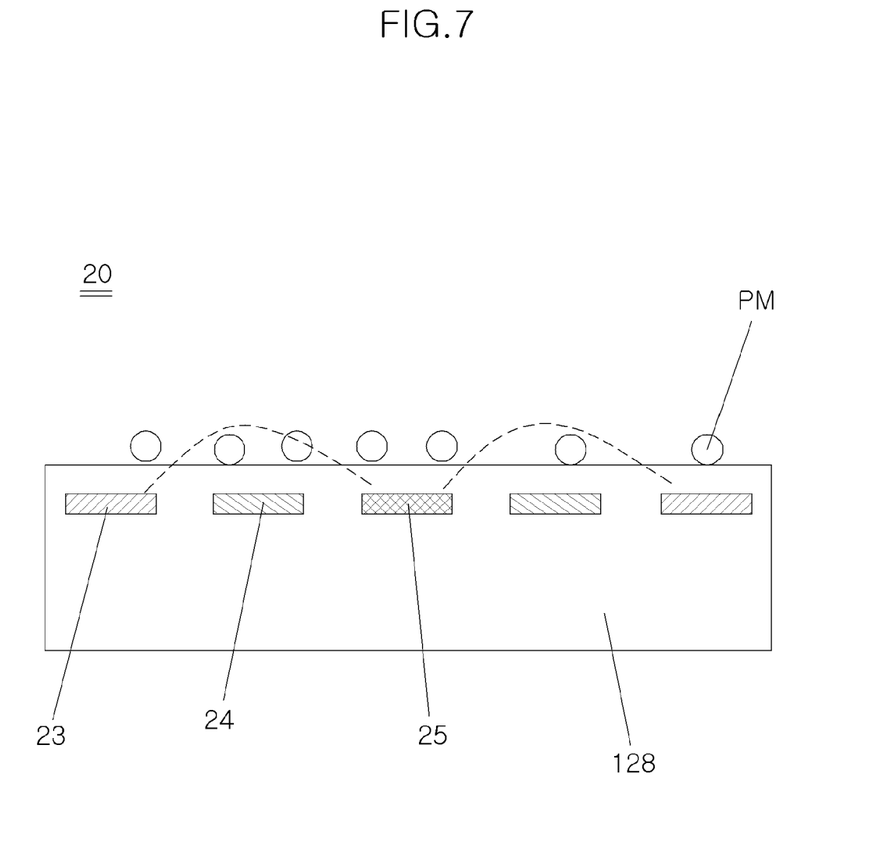
FIG. 7 is a cross-sectional view of a sensing unit of a sensor for measuring particulate matters with a bias voltage in accordance with one embodiment.

FIGS. 5 to 7 illustrate one embodiment of the disclosed sensors.

The sensing unit 20 included in the sensor for measuring particulate matters includes the ground electrodes 23 and the bias electrodes 25 that are disposed to alternate with one another, in which one terminal of the ground electrodes 23 is electrically connected to one another and one terminal of the bias electrodes 25 is also connected to one another.

The measurement electrodes 24 are disposed between the ground electrodes 23 and the bias electrodes 25, and are connected to one another in a zigzag form. The measurement electrode 24 is formed to enclose the bias electrode 25 or the ground electrode 23. The measurement electrode 24, the ground electrode 23, and the bias electrode 25 are disposed at the same height. There is commonality in that the measurement electrodes 24 are disposed between the ground electrodes 23.

The measurement electrode 24, the ground electrode 23, and the bias electrode 25 may be formed on the same layer in a ceramic layer. Because the measurement electrode 24, the ground electrode 23, and the bias electrode 25 are formed on the same layer, the bias electrode 25 may be implemented only by modifying a patterning mask during the existing process of patterning the sensing unit (see FIG. 6). In FIG. 6, the measurement electrode 24, the ground electrode 23, and the bias electrode 25 are patterned on a top layer. For example, in FIG. 6, the measurement electrode 24, the ground electrode 23, and the bias electrode 25 are patterned so that they are disposed at a portion indicated with a circle A while alternating with one another, thereby forming the sensing unit 20.

The measurement electrode 24, the ground electrode 23, and the bias electrode 25 all are not directly exposed to exhaust gas, and therefore may be made of molybdenum (Mo) as a material. By doing so, the measurement electrode 24, the ground electrode 23, and the bias electrode 25 may avoid the use of expensive platinum (Pt).

Figure 10:
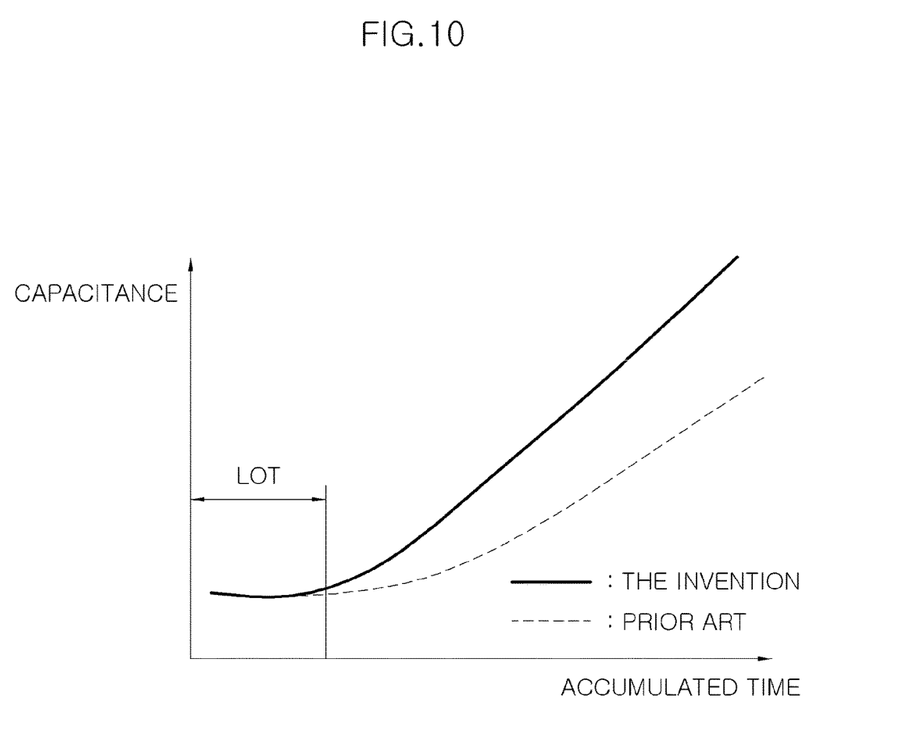
FIG. 10 is a graph illustrating a change in capacitance as a function of accumulated time in a sensor for measuring particulate matters with a bias voltage in accordance with one embodiment.

If power is supplied to the sensing unit 20, as illustrated in FIG. 7, an electric field is generated between the ground electrode 23 and the bias electrode 25 and thus the accumulated amount of particulate matters is increased due to the generated electric field. By supplying the bias voltage to the bias electrode 25 through a switching circuit, the accumulated amount of particulate matters is increased in the sensing unit 20 of the sensor for measuring particulate matters and a lift-off time (LOT) to generate an initial signal from the sensor for measuring particulate matters is reduced. Further, capacitance is more quickly increased with the accumulated time (see FIG. 10). Past sensors supply a bias voltage (for example, 30 V) between the measurement electrode and a ground and then supplies a measurement voltage (for example, 2V) between the measurement electrode and the ground to measure the capacitance and continuously repeats the above process. In contrast, the disclosed sensors supply the bias voltage (for example, 30 V) between the bias electrode 25 and the ground electrode 23 and supply the measurement voltage between the measurement electrode 24 and the ground electrode 23 to measure the capacitance, continuously repeating the above process. In some cases, the bias voltage is applied to the bias electrode through the switching circuit to avoid reducing a measurement area.

In FIG. 6, in the sensing unit 20, a heater 27 for increasing temperature is provided in the measurement electrode 24, the ground electrode 23, and the bias electrode 25. The measurement electrode 24, the ground electrode 23, and the bias electrode 25 are formed on one layer. The heater 27 is patterned on a layer disposed under the layer on which the measurement electrode 24, the ground electrode 23, and the bias electrode 25 are formed. A temperature sensor 26 for measuring the temperature of the heater 27 is disposed under the layer on which the heater 27 is formed, a substrate 21 is disposed thereunder, and one side is formed with a pad electrode 22 that electrically connect between the layers. The heater 27 increases the temperature at initial operation to remove moisture present on a surface of the sensing unit 20. Further, if the temperature of the heater 27 rises to a particulate matter (PM) regeneration temperature (for example, 650° C.) or more, the particulate matter accumulated on the surface of the sensing unit 20 may be regenerated.

Figure 8:
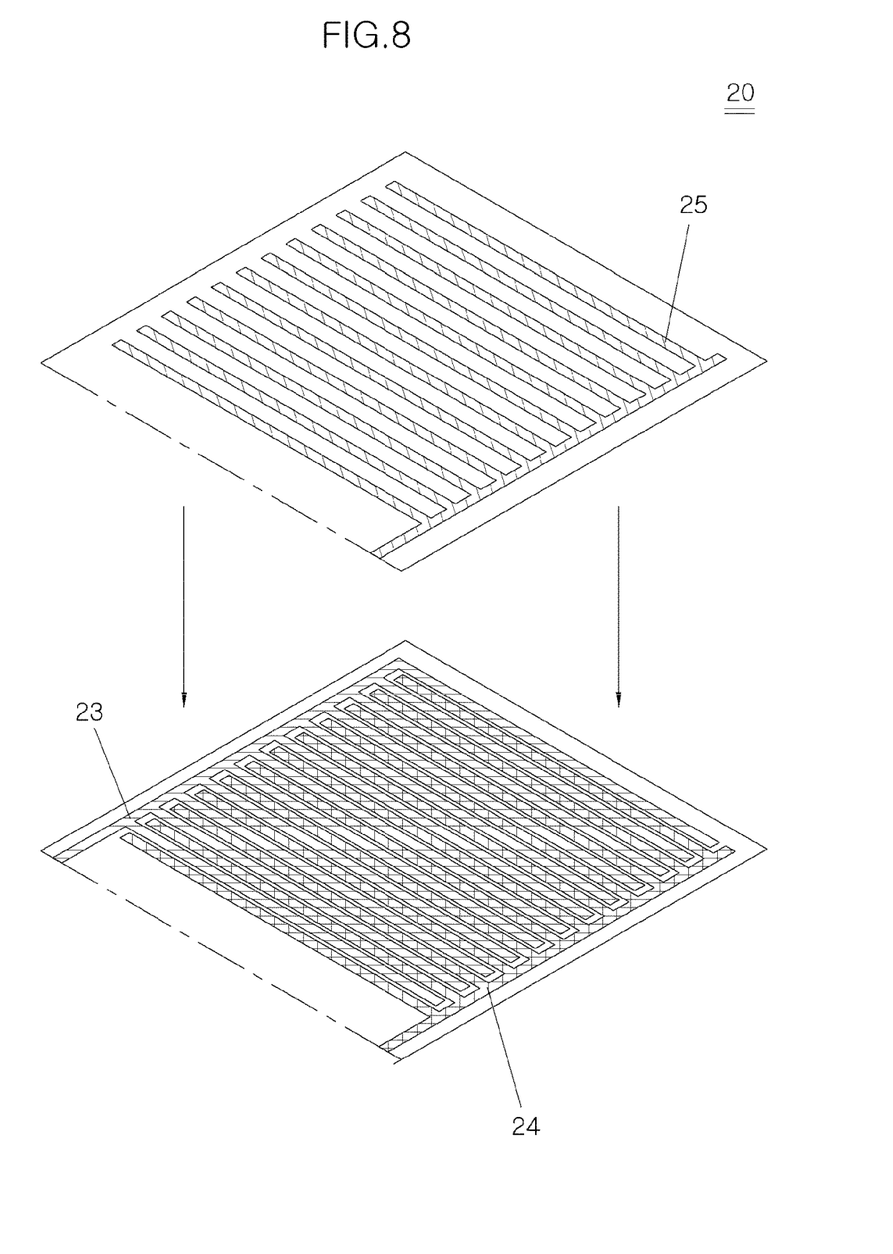
FIG. 8 is an exploded perspective view of a sensing unit of a sensor for measuring particulate matters with bias voltage in accordance with another embodiment.
Figure 9:
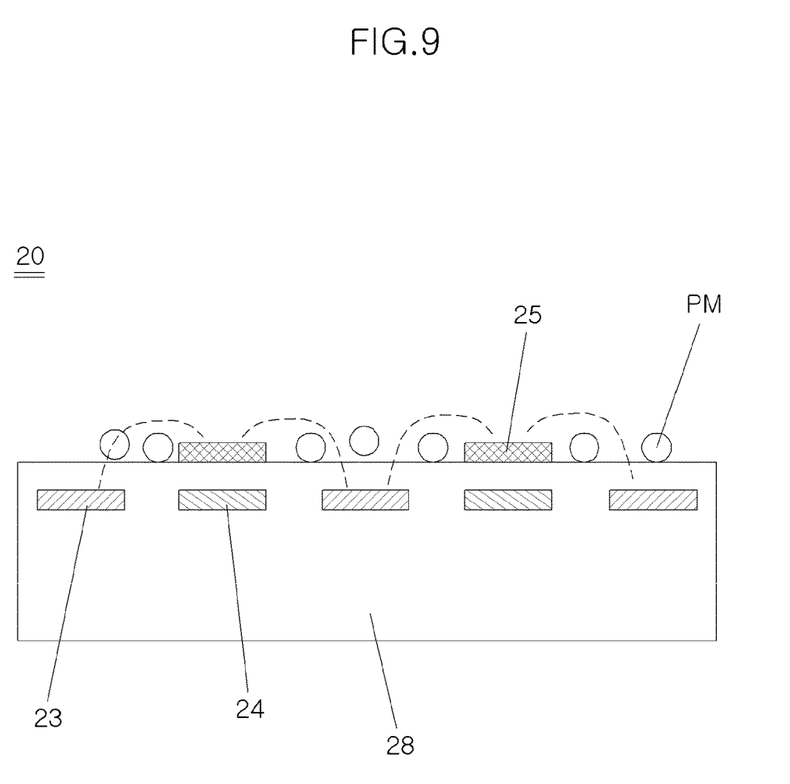
FIG. 9 is a cross-sectional view of the sensing unit of the sensor of FIG. 8.

Meanwhile, FIGS. 8 and 9 illustrate another embodiment of the disclosed sensors.

According to this embodiment, among the electrodes configuring the sensing unit 20, the measurement electrode 24 and the ground electrode 23 are disposed at the same height. The measurement electrodes 24 and the ground electrodes 23 are disposed to alternate with one another, in which one terminal of the measurement electrodes 24 is electrically connected to one another and one terminal of the ground electrodes 23 are electrically connected to one another.

The bias electrode 25 is formed in the same pattern as the measurement electrode 24 and is located above the measurement electrode 24 (see FIG. 8).

The measurement electrode 24 and the ground electrode 23 are formed in the ceramic layer, and the bias electrode 25 is formed on the surface of the ceramic layer.

The measurement electrode 24 and the ground electrode 23 are not directly exposed to exhaust gas and therefore may be made of molybdenum (Mo) as a material. The bias electrode 25 exposed to the exhaust gas is made of platinum (Pt) as a material. Cost savings are achieved with the measurement electrode 24 and the ground electrode 23 not made of expensive platinum (Pt) and only the bias electrode 25 made of only platinum (Pt).

According to one embodiment, if the bias voltage is applied to the bias electrode 25, as illustrated in FIG. 9, the amount of particulate matters accumulated in the sensing unit 20 is increased while the electric field is formed between the ground electrode 23 and the bias electrode 25 to increase the capacitance while reducing the time (LOT) required to generate the initial signal.

In some embodiments of the disclosed sensors for measuring particulate matters, a protective tube 30 is disposed at a lower end of the housing 11 to protect the sensing unit 20 from foreign materials.

Figure 11:
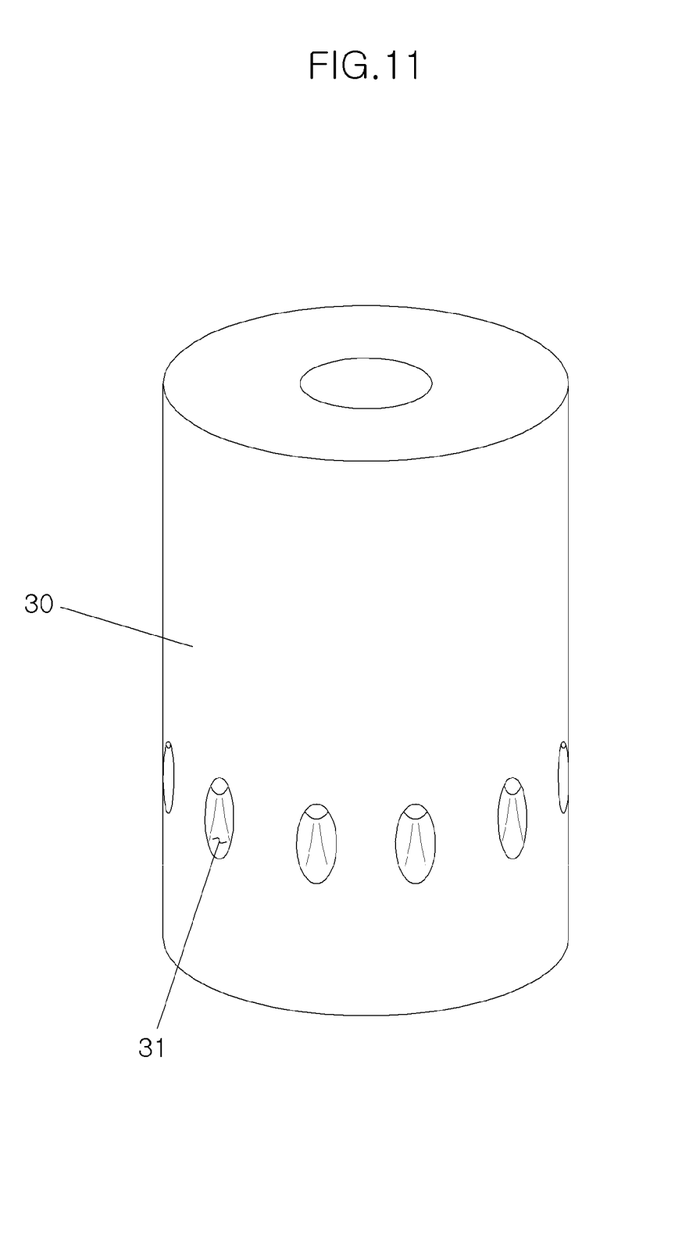
FIG. 11 is a perspective view of a protective tube of a sensor for measuring particulate matters with a bias voltage in accordance with one embodiment.
Figure 12:
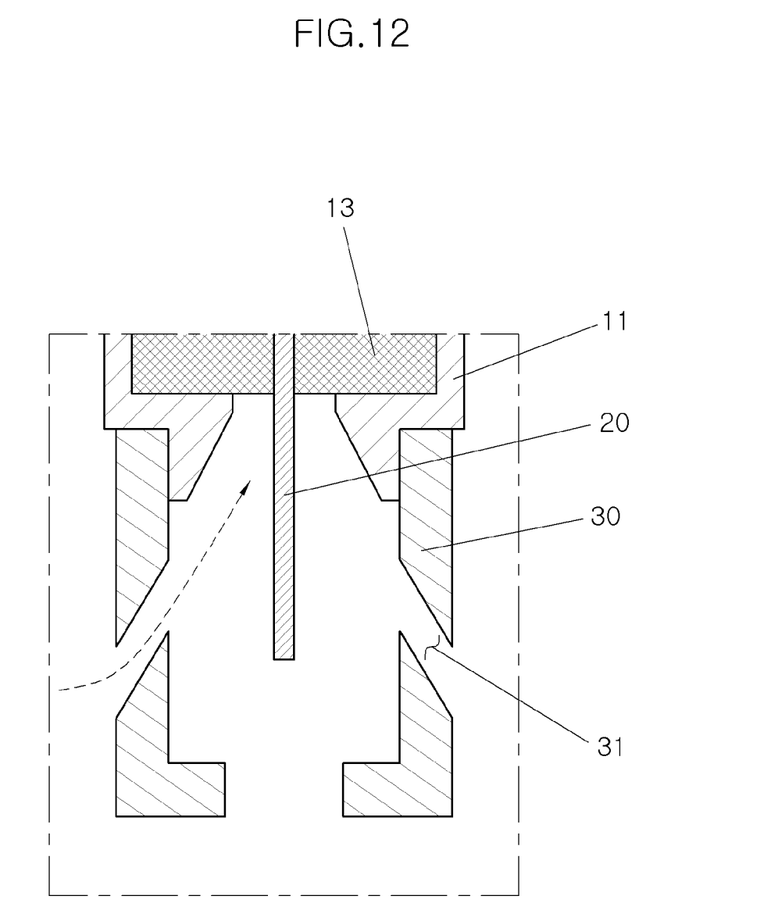
FIG. 12 is an enlarged, cross-sectional, partial view of a sensor for measuring particulate matters with a bias voltage, the sensor having a protective tube mounted therein in accordance with one embodiment.

The protective tube 30 has a cylindrical shape. As illustrated in FIGS. 11 and 12, the protective tube 30 has introduction holes 31 disposed along a circumference thereof to directly introduce the exhaust gas flowing in the exhaust pipe 1 into the sensing unit 20. The introduction hole 31 is formed to be upwardly inclined inwardly from an outer side surface of the protective tube 30 to directly introduce the exhaust gas into the sensing unit 20. The introduction hole 31 is formed to be inclined upwardly and thus the flow of the exhaust gas is concentrated on the sensing unit 20.

The introduction hole 31 may be formed in plural at a predetermined interval along the circumference of the protective tube 20.

Figure 13:
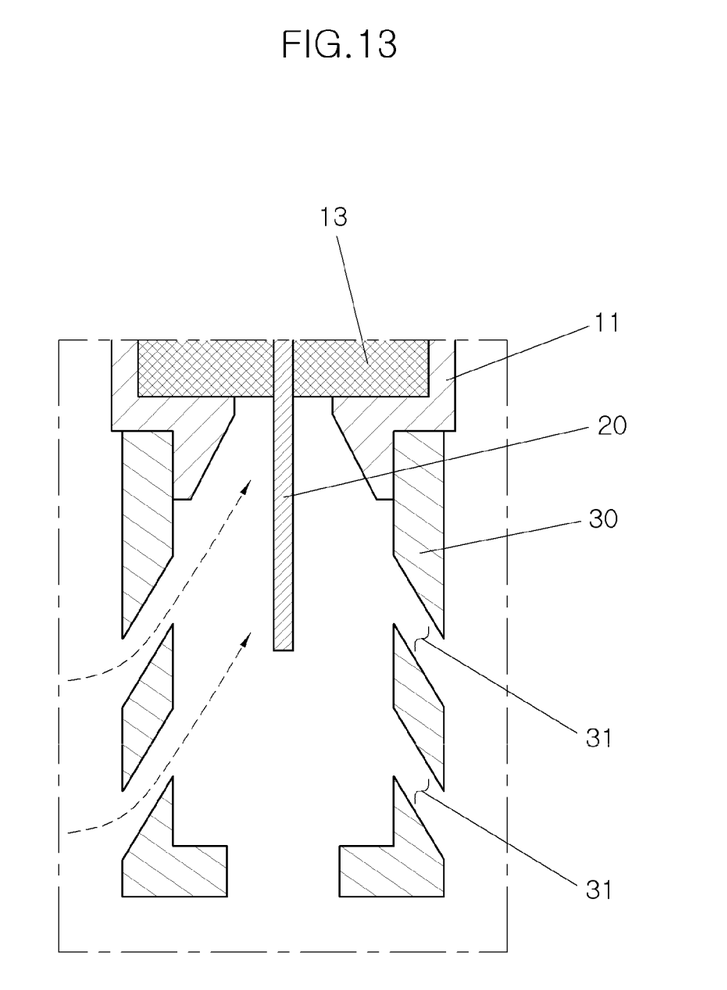
FIG. 13 is an enlarged, cross-sectional, partial view of a sensor for measuring particulate matters with a bias voltage, the sensor having a protective tube mounted therein in accordance with another embodiment.

Further, as illustrated in FIG. 13, the introduction hole 31 may also be formed in a plurality of rows along a length direction of the protective tube 30.

In embodiments of the disclosed sensors for measuring particulate matters with a bias voltage having the above-described structure, the electric field may be efficiently formed by supplying the bias voltage by the bias electrode to increase the amount of particulate matters accumulated in the same area.

Further, the bias electrode may shorten the initial signal generation time by applying the bias voltage to the sensing unit.

Further, the flowing exhausting gas may be directly introduced concentratedly into the sensing unit by the introduction hole formed to be upwardly inclined on the side of the protective tube to accurately measure the amount of particulate matters, thereby determining whether the diesel particulate filter (DPF) fails.

The cost of the sensor for measuring particulate matters may be reduced as a result of not using platinum as an electrode material or as a result of reducing the amount of platinum consumed.

The foregoing embodiments are only examples to allow a person having ordinary skill in the art to which the present disclosure pertains (hereinafter, referred to as "those skilled in the art") to practice the present disclosure. Accordingly, the present disclosure is not limited to the foregoing embodiments and the accompanying drawings, and therefore, a scope of the present disclosure is not limited to the foregoing embodiments. Accordingly, it will be apparent to those skilled in the art that substitutions, modifications and variations can be made without departing from the spirit and scope of the disclosure as defined by the appended claims.

What is claimed is:

1. A sensor for measuring particulate matters in exhaust gas, the sensor comprising:
   a sensing unit in which measurement electrodes and ground electrodes are disposed to alternate with one another in a housing fixed to an exhaust pipe, wherein the measurement electrodes are electrically connected to one another, and wherein the ground electrodes are electrically connected to one another; and
   bias electrodes disposed between the ground electrodes to supply a bias voltage to the sensing unit;
   wherein the bias electrodes are electrically connected to one another.

2. The sensor of claim 1, wherein:
   each of the bias electrodes is disposed between the ground electrodes at the same height as the ground electrodes;
   the measurement electrodes are disposed between the bias electrodes and the ground electrodes adjacent to one another at the same height as the bias electrodes and the ground electrodes; and
   the measurement electrodes are connected to one another in a zigzag shape.

3. The sensor of claim 2, wherein the measurement electrodes, the ground electrodes, and the bias electrodes are disposed in a ceramic layer.

4. The sensor of claim 3, wherein the measurement electrodes, the ground electrodes, and the bias electrodes comprise molybdenum (Mo).

5. The sensor of claim 1, wherein:
   the bias electrodes are disposed in the same pattern as the measurement electrodes; and
   the bias electrodes are located above the measurement electrodes.

6. The sensor of claim 5, wherein:
the measurement electrodes and the ground electrodes are disposed in a ceramic layer; and
the bias electrodes are disposed on a surface of the ceramic layer.

7. The sensor of claim 6, wherein:
the measurement electrodes and the ground electrodes comprise molybdenum; and
the bias electrodes comprise platinum (Pt).

8. The sensor of claim 1, wherein:
the sensing unit comprises a heater patterned on a layer disposed under a layer on which the measurement electrodes, the ground electrodes, and the bias electrodes are disposed to increase a temperature of the sensing unit; and
the sensor further comprises a temperature sensor configured to measure a temperature of the heater, the temperature sensor being disposed on a layer under the layer on which the heater is disposed.

9. The sensor of claim 1, further comprising a protective tube having a cylindrical shape and comprising introduction holes that are disposed to be upwardly inclined along a circumference of the protective tube, wherein:
the introduction holes penetrate through an inside of the protective tube from an outside of the protective tube and are disposed at a predetermined interval along the circumference of the protective tube;
the protective tube is fastened with a lower end of the housing; and
the exhaust gas flowing in the exhaust pipe flows in the sensing unit through the introduction holes.

10. The sensor of claim 9, wherein the introduction holes are disposed in a plurality of rows along a length direction of the protective tube.

* * * * *